US006680418B2

(12) United States Patent
Brown

(10) Patent No.: US 6,680,418 B2
(45) Date of Patent: Jan. 20, 2004

(54) PROCESS FOR PRODUCING LIGHT OLEFINS

(75) Inventor: Stephen H. Brown, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 53 days.

(21) Appl. No.: 10/023,025

(22) Filed: Oct. 30, 2001

(65) Prior Publication Data

US 2002/0091292 A1 Jul. 11, 2002

Related U.S. Application Data

(60) Provisional application No. 60/252,231, filed on Nov. 21, 2000.

(51) Int. Cl.$^7$ .................................................. C07C 1/00
(52) U.S. Cl. ........................................ 585/639; 585/640
(58) Field of Search ................................ 585/640, 639

(56) References Cited

U.S. PATENT DOCUMENTS

| | | | |
|---|---|---|---|
| 3,702,886 A | 11/1972 | Argauer et al. | 423/328 |
| 3,709,979 A | 1/1973 | Chu | 423/328 |
| 3,832,449 A | 8/1974 | Rosinski, et al. | 423/328 |
| 4,016,218 A | 4/1977 | Haag et al. | 260/671 R |
| 4,016,245 A | 4/1977 | Plank et al. | 423/328 |
| 4,025,575 A | 5/1977 | Chang et al. | 260/682 |
| 4,038,889 A | 8/1977 | Lindow et al. | 74/866 |
| 4,076,842 A | 2/1978 | Plank et al. | 423/328 |
| 4,079,095 A | 3/1978 | Givens et al. | 260/682 |
| 4,375,573 A | 3/1983 | Young | 585/467 |
| 4,499,314 A | 2/1985 | Seddon et al. | 585/408 |
| 4,520,219 A | 5/1985 | Sato | 585/462 |
| 4,582,815 A | 4/1986 | Bowes | 502/64 |
| 4,677,242 A | 6/1987 | Kaiser | 585/638 |
| 4,752,651 A | 6/1988 | Kaiser | 585/640 |
| 5,043,503 A | 8/1991 | Del Rossi et al. | 585/360 |
| 5,053,374 A | 10/1991 | Absil et al. | 502/64 |
| 5,095,167 A | 3/1992 | Christensen | 585/720 |
| 5,182,242 A | 1/1993 | Marler | 502/66 |
| 5,250,277 A | 10/1993 | Kresge et al. | 423/329.1 |
| 5,304,698 A | 4/1994 | Hussain | 585/722 |
| 6,046,372 A * | 4/2000 | Brown et al. | 585/640 |

FOREIGN PATENT DOCUMENTS

WO  WO 99/51548  10/1999  ............. C07C/1/00

OTHER PUBLICATIONS

Olson, D.H., et al, "Chemical and Physical Properties of the ZSM–5 Substitutional Series," *Journal of Catalysis*, vol. 61, pp. 390–396 (1980).

* cited by examiner

Primary Examiner—Walter D. Griffin
Assistant Examiner—Tam M. Nguyen

(57) ABSTRACT

There is provided a process for converting methanol and/or dimethyl ether to a product containing $C_2$ to $C_4$ olefins which comprises the step of contacting a reaction mixture which contains methanol and/or dimethyl ether and at least 10 wt % of a polymethylbenzene component selected from trimethylbenzenes, tetramethylbenzenes and mixtures thereof with a catalyst comprising a porous crystalline material. The contacting step is conducted under conversion conditions including a temperature of about 250° C. to about 500° C. and a methanol and/or dimethyl ether partial pressure of about 5 to about 250 psia (35 to 1725 kPa). The porous crystalline material used in the catalyst has a pore size greater than the critical diameter of the aromatic compound and a Diffusion Parameter for 2,2-dimethylbutane of at least 500 sec$^{-1}$ when measured at a temperature of 120° C. and a 2,2-dimethylbutane pressure of 60 torr (8 kPa).

11 Claims, No Drawings

PROCESS FOR PRODUCING LIGHT OLEFINS

CROSS REFERENCE TO RELATED APPLICATIONS

This application claims the benefit of U.S. Provisional Application No. 60/252,231, filed on Nov. 21, 2000.

FIELD OF THE INVENTION

The present invention relates to a process for producing light olefins rich in ethylene from methanol and dimethyl ether.

BACKGROUND TO THE INVENTION

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, and other, four and five carbon olefins. Side by side with this growth, there has been an increasing demand for alkylate, made by reacting olefins with isobutane, for use as a high octane gasoline component.

Burgeoning demand for olefins, particularly ethylene, propylene and butenes, has of course led to periods of shortage, which has led to substantial price increases in the feedstocks to the commercialized technologies. These feedstocks are largely $C_2$ to $C_4$ olefins co-produced with natural gas and/or paraffinic straight run naphtha. These feedstocks can be substantially more expensive than methane, making it desirable to provide efficient means for converting methane to olefins.

Conversion of methane to methanol followed by conversion of methanol to light olefins is among the most economic routes to make light olefins from methane. In this respect, it is known that methanol or methyl ether can be catalytically converted to olefin-containing hydrocarbon mixtures by contact under certain conditions with particular types of crystalline zeolite materials. U.S. Pat. Nos. 4,025,575 and 4,038,889 for example, both disclose processes whereby methanol and/or methyl ether can be converted to an olefin-containing product over a Constraint Index 1–12 zeolite catalyst, particularly ZSM-5. ZSM-5, in fact, converts methanol and/or methyl ether to hydrocarbons containing a relatively high concentration of light olefins with prolonged catalyst lifetime before catalyst regeneration becomes necessary.

It has also been reported that other types of zeolite catalysts can be used to convert methanol and/or methyl ether to olefin-containing hydrocarbons products containing even higher proportions of light olefins than obtained with ZSM-5. For example, U.S. Pat. No. 4,079,095 discloses that zeolites of the erionite-offretite-chabazite type, and especially ZSM-34, can usefully be employed to promote conversion of methanol and/or methyl ether to products comprising a major amount of ethylene and propylene. However, while erionite-offretite-chabazite type catalysts are highly selective to light olefins production, such smaller pore zeolites tend to age rapidly in comparison to ZSM-5 when used for methanol/methyl ether conversion.

U.S. Pat. Nos. 4,677,242 and 4,752,651 disclose the conversion of methanol to $C_2$–$C_4$ olefins over various silicoaluminophosphates and "non-zeolitic molecular sieves" (such as metal aluminophosphates) and teach that the addition of diluents, such as aromatic materials, having a kinetic diameter greater than the pore size of the molecular sieve increases the ethylene to propylene ratio in the product.

U.S. Pat. No. 4,499,314 discloses that the addition of various promoters, including aromatic compounds, such as toluene, accelerate the conversion of methanol to hydrocarbons over zeolites, such as ZSM-5, which have a pore size sufficient to permit sorption and diffusion of the promoter. In particular, the '314 patent teaches that the increased conversion resulting from the addition of the promoter allows the use of lower severity conditions, particularly lower temperatures, which increase the yield of lower olefins (column 4, lines 17–22). However, the Examples of the '349 patent employ ZSM-5 with a large crystal size, namely in excess of 1 micron (see column 13, lines 60–65). Surprisingly, it has now been found that small crystal ZSM-5 (as defined by having a Diffusion Parameter for 2,2-dimethylbutane of at least 500 $sec^{-1}$) can, in the presence of tetramethylbenzene and under closely controlled conditions, selectively convert methanol to $C_2$ to $C_4$ olefins.

U.S. Pat. No. 4,520,219 discloses a process for producing pseudocumene or durene by reacting xylene with methanol over a catalyst comprising at least one crystalline silicate selected from the group consisting of a crystalline borosilicate, a fluorine-containing crystalline borosilicate, a fluorine-containing crystalline aluminosilicate and a fluorine-containing crystalline boroaluminosilicate. According to Example 8 of the '219 patent, using fluorine-containing aluminosilicate ZSM-5 to methylate xylene at 300° C. and 9 kg/cm² in a two-reactor system gives a product in which the $C_9$ and $C_{10}$ components consist mainly of pseudocumene and durene, respectively, and an unspecified amount of a gaseous component is produced consisting mainly of ethylene and propylene. However, since the object of the process described in the '219 patent is to enhance the yield of polymethylated benzenes by maximizing methylation of the xylene and minimizing decomposition of the methylating agent, no incentive exists to recycle the polymethylated benzene product in an attempt to increase the yield of olefins.

SUMMARY OF THE INVENTION

The present invention resides in a process for converting methanol and/or dimethyl ether to a product containing $C_2$ to $C_4$ olefins which comprises the step of contacting a reaction mixture which contains methanol and/or dimethyl ether and at least 10 wt % of a polymethylbenzene component selected from trimethylbenzenes, tetramethylbenzenes and mixtures thereof with a catalyst comprising a porous crystalline material, the contacting step being conducted under conversion conditions including a temperature of about 250° C. to about 500° C. and a methanol and/or dimethyl ether partial pressure of about 5 to about 250 psia (35 to 1725 kPa), and the porous crystalline material having a Diffusion Parameter for 2,2-dimethylbutane of at least 500 $sec^{-1}$ when measured at a temperature of 120° C. and a 2,2-dimethylbutane pressure of 60 torr (8 kPa).

Preferably, the polymethylbenzene component comprises at least 10 wt %, and more preferably at least 30 wt %, of at least one tetramethylbenzene.

Preferably, the process includes the further steps of introducing into the reaction mixture an aromatic compound which is selected from the group consisting of benzene, toluene, xylene, a trimethylbenzene and mixtures thereof and which is capable of alkylation by the methanol and/or dimethyl ether under the conversion conditions, and recycling to the contacting step a trimethylbenzene- and/or tetramethylbenzene-containing fraction of said product.

Preferably, the molar ratio of methanol and/or dimethyl ether to the aromatic compound is from about 0.1:1 to about 25:1, and more preferably from about 1:1 to about 10:1.

Preferably, the conversion conditions include a temperature of about 250° C. to about 400° C.

Preferably, the conversion conditions are such that the methanol conversion rate is less than 90% and more preferably less than 80%.

Preferably, the porous crystalline material has a pore size between 5 and 7 Angstrom.

Preferably, the porous crystalline material is an aluminosilicate zeolite which is substantially free of fluorine and most preferably is ZSM-5.

Preferably, the catalyst has an alpha value less than 250 and more preferably less than 150.

Preferably, the porous crystalline material has a Diffusion Parameter for 2,2-dimethylbutane of about 500 to about 2000 sec$^{-1}$ when measured at a temperature of 120° C. and a 2,2-dimethylbutane pressure of 60 torr (8 kPa).

DETAILED DESCRIPTION OF THE INVENTION

The present invention provides a catalytic process for selectively converting methanol and/or dimethyl ether to $C_2$–$C_4$ olefins in a reaction mixture which contains at least 10 wt % of a polymethylbenzene component selected from trimethylbenzenes, tetramethylbenzenes and mixtures thereof. The catalyst employed in the process of the invention contains a porous crystalline material which has a Diffusion Parameter for 2,2-dimethylbutane of at least 500 sec$^{-1}$, and preferably about 500 to about 2000 sec$^{-1}$, when measured at a temperature of 120° C. and a 2,2-dimethylbutane pressure of 60 torr (8 kPa). In the preferred embodiment, in which the porous crystalline material is ZSM-5, the required Diffusion Parameter is achieved by using a material having a crystal size of about 0.02 to about 0.1 micron.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value Q/Q∞, where Q∞ is the equilibrium sorbate loading and is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

Using small crystal ZSM-5 to effect methanol conversion in a reaction mixture containing at least 10 wt % of a polymethylbenzene component selected from trimethylbenzenes, tetramethylbenzenes and mixtures thereof at a temperature within the range of about 250° C. to about 500° C., more preferably about 250° C. to about 400° C., and a methanol partial pressure within the range of about 5 to about 250 psia (35 to 1725 kPa) such that the methanol conversion is less than 90%, and more preferably less than 80%, it has been found that ethylene and propylene selectivities in excess of 30 wt % can be achieved.

Any methanol feed comprising at least 60 wt % of methanol may be used to provide methanol for the use in this invention. Substantially pure methanol, such as industrial grade anhydrous methanol, is eminently suitable. Crude methanol, which usually contains from 12 to 20 wt % water, or even a more dilute solution, may also be used. However, the presence of water as a diluent to reduce the methanol partial pressure is not required. Trace amounts (<1% by weight) of non-aromatic organic impurities, such as higher alcohols, aldehydes, or other oxygenated compounds have little effect on the conversion reaction of this invention and may be present in the methanol feed.

In place of, or in addition to methanol, the non-aromatic reactant feed may comprise dimethyl ether. When this component is present, it can comprise up to 100% of the non-aromatic organic reactant feed or dimethyl ether can be admixed with methanol to form the non-aromatic reactant feed. For purposes of the present invention, it is contemplated to directly convert methanol and/or methyl ether in the feed to a hydrocarbon mixture characterized by a high content of light olefins, especially ethylene and propylene. Such amounts of dimethyl ether as may be formed concomitantly in the conversion reaction, however, may be recovered and recycled with fresh organic reactant feed.

In addition to methanol and/or dimethyl ether, the reaction mixture used in the process of the invention contains at least 10 wt % of a polymethylbenzene component selected from trimethylbenzenes, tetramethylbenzenes and mixtures thereof. Preferably, the polymethylbenzene component comprises at least 10 wt %, and more preferably at least 30 wt %, of at least one tetramethylbenzene, preferably durene. The polymethylbenzene component can be added as a fresh feed or more preferably is introduced as a recycle stream generated by cofeeding an aromatic compound, which has a critical diameter less than the pore size of the catalyst and which is capable of alkylation by the methanol and/or dimethyl ether to tetramethylbenzene under the process conditions, and then extracting from the product a trimethylbenzene- and/or tetramethylbenzene-containing fraction.

Suitable aromatic compounds for use as the cofeed are selected from the group consisting of benzene, toluene, xylene, a trimethylbenzene and mixtures thereof and can come from a wide variety of sources. Even substantial amounts of non-aromatic organic components have little impact on the role of the aromatic co-feed. For this reason, any organic feedstream containing >10 wt % of the required aromatic compound, is suitable for use in the process of the invention. These include, but are not limited to, C9+ reformate streams, light reformates, full-range reformates or any distilled fraction thereof, coker naphtha or any distilled fraction thereof, FCC naphtha or any distilled fraction thereof, steam cracked naphtha or any distilled fraction thereof, and coal derived aromatics. Part of the required aromatic compound can also be produced in-situ by aromatization of the methanol feed, although in general some co-feeding of the aromatic compound with the methanol appears to be important. The presence of impurities, such as nitrogen and sulfur compounds, dienes and styrenes, in the aromatic component can be tolerated with little impact when fluid or moving bed embodiments of the invention are employed.

The molar ratio of methanol and/or dimethyl ether to aromatic compound will normally be greater than 0.1:1, since higher concentrations of aromatic compound lead to excessive coking, increased volumes of separation and recycle traffic and minimal gains in total chemical selectivities. Moreover the molar ratio of methanol and/or dimethyl ether to aromatic compound is normally maintained below 25:1, since lower concentrations of aromatic compound lead to little or no noticeable improvement in the ethylene selectivity of the process. Preferably the molar ratio of methanol and/or dimethyl ether to aromatic compound is from about 1:1 to about 10:1.

The catalyst employed in the process of the invention is a porous crystalline material which has a pore size greater than the critical diameter of the aromatic compound co-feed. Preferred catalysts are porous crystalline materials having a pore size between 5 and 7 Angstrom and in particular intermediate pore size, aluminosilicate zeolites. Preferably, the zeolites are free of fluorine and boron. One common definition for intermediate pore zeolites involves the Constraint Index test which is described in U.S. Pat. No. 4,016,218, which is incorporated herein by reference. In this case, intermediate pore zeolites have a Constraint Index of about 1–12, as measured on the zeolite alone without the introduction of modifiers and prior to any treatment to adjust the diffusivity of the catalyst. In addition to the medium-pore size aluminosilicates, other medium pore acidic metallosilicates, such as silicoaluminophosphates (SAPOs), can be used in the process of the invention.

Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. No. 5,304,698 to Husain; U.S. Pat. No. 5,250,277 to Kresge et al.; U.S. Pat. No. 5,095,167 to Christensen; and U.S. Pat. No. 5,043,503 to Del Rossi et al., the disclosure of which patents are incorporated by reference.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20 to 200 microns.

Using the alpha test of acid activity disclosed in *Journal of Catalysis,* volume 61, page 395 (1980), the entire disclosure of which is incorporated by reference herein, the catalyst of the invention preferably has an alpha value less than 250, more preferably less than 150. Where necessary, the alpha value of the catalyst can be reduced to the desired value by methods known in the art, such as steaming at temperatures of 350 to 500° C.

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a temperature between about 250° C. and 500° C., preferably between about 250° C. and 400° C., and a methanol partial pressure of about 5 to about 250 psia (35 to 1725 kPa), preferably 30 to 120 psia (205 to 830 kPa). In addition, it is desirable that the conversion conditions are controlled so that the methanol conversion level is less than about 90% and preferably less than 80% since, at higher conversion levels, competing reactions to aromatics methylation, such as olefin alkylation and/or oligomerizarion to produce $C_5+$ isoolefins and/or olefin conversion to aromatics and paraffins, lower the selectivity to ethylene and propylene. Suitable control of the methanol conversion can, of course, be achieved by variation of the weight hourly space velocity, which typically can vary between about 0.1 and 100, preferably between about 0.1 and 10.

The invention will now be more particularly described with reference to the following Examples. In the Examples, the experiments were conducted in a downflow fixed-bed unit in which a 18 inch (46 cm) long, ½ inch (1.3 cm) outside diameter, quartz reactor with ⅛ inch (0.3 cm) outside diameter internal quartz thermowell was centered inside a 10 inch (46 cm) long, single-zone furnace. Methanol and aromatic feedstocks were obtained from Aldrich and used as received. Distilled water was produced in-house. The feeds were introduced using two Isco high-pressure positive displacement pumps. Aromatics and methanol were blended in the desired molar ratio and delivered from one pump, while the second pump was used to deliver distilled water. ¹/₁₆ inch (16 mm) tubing was used to deliver each feedstock to a single, 250-cc vaporizer which was heat-traced and held at 220° C. Vaporized feed flowed from the vaporizer through the reactor, into a 300-cc product back-mixing vessel, through an on-line GC equipped with a 60-m DBWax column and an FID detector, and into a product collection can held at room temperature. Any gases produced flowed through the product collection can and finally through a wet test meter. All feed and product lines upstream of the GC sampling were held above 200° C. using heat tracing. The unit back-pressure was controlled with a Grove Loader. On-line total product GC was used to determine product composition.

EXAMPLE 1

A ZSM-5 catalyst, comprising 65 wt % of 26:1 $SiO_2:Al_2O_3$ molar ratio ZSM-5 having a crystal size of about 0.02 micron, that had been steamed at 950° F. (510° C.) for 1 hour, was used to convert methanol at 275° C. and 1 atmosphere pressure. The steamed catalyst had a Diffusion Parameter of 3000, an n-hexane sorption of 65 mg/g and an alpha of about 100. The hydrocarbon selectivity at partial methanol conversion is reported in Table 1.

EXAMPLE 2

The steamed catalyst of Example 1 was used to convert a mixture of 50 wt % methanol and 50 wt % xylene (methanol:xylene molar ratio of 3:1) at 275° C. and 1 atm. The non-aromatic hydrocarbon selectivity at partial methanol conversion is reported in Table 1. It will be seen from the results in Table 1 that the addition of the aromatic cofeed produced a marked increase in the propylene selectivity without significant change in the ethylene selectivity. The process also produced a significant quantity of durene which could be recycled.

EXAMPLE 3

A ZSM-5 catalyst comprising 65 wt % of 70:1 $SiO_2:Al_2O_3$ molar ratio ZSM-5 having a crystal size of 0.5 micron was steamed at 950° F. (510° C.) for 1 hour. The steamed catalyst had a Diffusion Parameter of 8, an n-hexane sorption of 65 mg/g and an alpha value of about 200. The catalyst was contacted with a mixture of 90 wt % methanol and 10 wt % toluene (methanol:toluene molar ratio of 26:1) at 275° C. and 1 atm, but showed showed no activity for methanol conversion to hydrocarbons at these conditions.

Examples 1–3 leads to the unexpected conclusion that high $D/r^2$ ZSM-5's are more effective in the selective conversion of methanol to light olefins with aromatic co-feeds than low $D/r^2$ ZSM-5's.

EXAMPLE 4

Phosphoric acid, kaolin clay, and 50:1 $SiO_2:Al_2O_3$ molar ratio ZSM-5 is slurried in water, spray dried and calcined in air at 510° C. to make a fluid-bed catalyst containing 40 wt % ZSM-5 and 4.5 wt % phosphorus. The finished catalyst has a $D/r^2$ value of 3000, an alpha of 100, and an n-hexane sorption of 38 mg/gm. This catalyst is used to convert a feedstock of 50 wt % tetramethylbenzenes and 50 wt % methanol at 30 psig and 350° C. The methanol conversion and olefin selectivity were similar to Example 2, but with an improved yield of the light products. Less than 1% of the durene is converted to heavier aromatics.

TABLE 1

| Example | 1 | 2 |
|---|---|---|
| MeOH Conversion | 26 | 24 |
| Temperature | 275 | 275 |
| Product Composition, Wt % | | |
| Methane | 0.071 | 0.025 |
| Ethylene | 2.887 | 1.732 |
| Ethane | 0.000 | 0.009 |
| Propylene | 1.657 | 1.670 |
| Propane | 0.413 | 0.209 |
| Methanol/DME | 73.548 | 38.037 |
| Butenes | 0.340 | 0.492 |
| Butanes | 0.664 | 0.154 |
| C5—C9 Non-Aromatics | 1.417 | 0.332 |
| Isopentane | 1.092 | 0.194 |
| Benzene | 0.000 | 0.000 |
| Heptane | 0.000 | 0.000 |
| Toluene | 0.045 | 0.089 |
| EB | 0.000 | 0.063 |
| Xylenes | 0.456 | 40.686 |
| p-ethyltoluene | 0.043 | 0.096 |
| 1,2,4 TMB | 0.728 | 6.690 |
| Durene | 1.576 | 2.700 |
| Water | 15.063 | 6.824 |
| | 100.000 | 100.000 |
| Selectivity to Non Aromatics | | |
| Ethylene | 34% | 36% |
| Propylene | 19% | 35% |
| Butenes | 4% | 10% |
| C5—C9 Non-Aromatics | 29% | 11% |
| C1—C4 Paraffins | 13% | 8% |
| | 100% | 100% |

What is claimed is:

1. A process for converting methanol and/or dimethyl ether to a product containing $C_2$ to $C_4$ olefins which comprises the step of contacting a reaction mixture which contains methanol and/or dimethyl ether and at least 10 wt % of tetramethylbenzenes with a catalyst comprising a porous crystalline material, said contacting step being conducted under conversion conditions including a temperature of about 250° C. to about 500° C. and a methanol and/or dimethyl ether partial pressure of about 35 kPa to 1725 kPa, and said porous crystalline material having a Diffusion Parameter for 2,2-dimethylbutane of at least 500 sec$^{-1}$ when measured at a temperature of 120° C. and a 2,2-dimethylbutane pressure of 8 kPa.

2. The process of claim 1, wherein the polymethylbenzene component comprises at least 30 wt % of at least one tetramethylbenzene.

3. The process of claim 1 further comprising: introducing into said reaction mixture an aromatic compound selected from the group consisting of benzene, toluene, xylene, a trimethylbenzene and mixtures thereof and which is capable of alkylation by the methanol and/or dimethyl ether under the conversion conditions; and recycling to the step of contacting a trimethylbenzene and/or tetramethylbenzene-containing fraction of the product.

4. The process of claim 3 wherein the molar ratio of methanol and/or dimethyl ether to aromatic compound is from about 0.1:1 to about 25:1.

5. The process of claim 3 wherein the molar ratio of methanol and/or dimethyl ether to aromatic compound is from about 1:1 to about 10:1.

6. The process of claim 1 wherein the conversion conditions include a temperature of ranging from about 250° C. to about 400° C.

7. The process of claim 1 wherein the conversion conditions are such that the methanol conversion rate is less than 90%.

8. The process of claim 1 wherein the porous crystalline material has a pore size between 5 and 7 Angstrom.

9. The process of claim 1 wherein the porous crystalline material is ZSM-5.

10. The process of claim 1 wherein the porous crystalline material has a Diffusion Parameter for 2,2-dimethylbutane ranging from about 500 to about 2000 $sec^{-1}$ when measured at a temperature of 120° C. and a 2,2-dimethylbutane pressure of 8 kPa.

11. The process of claim 1 wherein the catalyst has an alpha value less than 150.

* * * * *